United States Patent [19]

Mikolajczak et al.

[11] Patent Number: 4,721,727
[45] Date of Patent: Jan. 26, 1988

[54] CONTROL OF PESTS WITH ANNONACEOUS ACETOGENINS

[75] Inventors: Kenneth L. Mikolajczak, Dunlap, Ill.; Jerry L. McLaughlin, West Lafayette, Ind.; James K. Rupprecht, Midland, Mich.

[73] Assignee: The United States of America as represented by the Secretary of Agriculture, Washington, D.C.

[21] Appl. No.: 860,351

[22] Filed: May 6, 1986

[51] Int. Cl.$^4$ .................... A01N 43/08; C07D 307/12
[52] U.S. Cl. .................................. 514/473; 549/320; 549/323
[58] Field of Search .................. 514/473; 549/320, 323

[56] References Cited

PUBLICATIONS

S. D. Jolad et al., "Uvaricin, a New Antitumor Agent from *Uvaria accuminata*, (Annonaceae)," J. Org. Chem. 47: 3151–3153, (1982).

S. D. Jolad et al., "Desacetyluvaricin from *Uvaria accuminata*, Configuration of Uvaricin at C-36," J. Nat. Prod. 48(4): 644–645, (Jul.–Aug. 1985).

T. T. Dabrah et al., "Rollinicin and Isorollinicin, Cytotoxic Acetogenins from *Rollinia papilionella*," Phytochemistry 23(9): 2013–2016, (1984).

T. T. Dabrah et al., "Rollinone, a New Cytotoxic Acetogenin from *Rollinia papilionella*," J. Nat. Prod. 47(4): 652–657, (Jul.–Aug. 1984).

D. Cortes et al., "Cherimoline et Dehydrocherimoline, etc" TL, 25, 3199, (1984).

El-Zayat, A. et al., "Goniothalenol: a Novel, etc" TL, 26, 955, (1985).

Rupprecht et al., "Asimicin, a New Cytotoxic, etc." 1986, CA 105: 39355f, 1986.

*Primary Examiner*—Glennon H. Hollrah
*Assistant Examiner*—Patricia L. Morris
*Attorney, Agent, or Firm*—M. Howard Silverstein; David G. McConnell; Curtis P. Ribando

[57] ABSTRACT

Tetrahydrofuranoid acetogenins characteristic of the Annonaceae plant family have been found to have potent pesticidal and feeding deterrent activity against a diverse variety of pests such as mosquito larvae, spider mites, aphids, the Mexican bean beetle, striped cumcumber beetle, blowfly larvae, and nematodes. A new acetogenin called "asimicin" having the following structural formula has been isolated and is typical of the subject class of useful compounds:

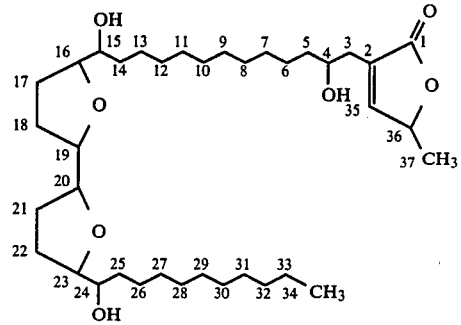

13 Claims, No Drawings

CONTROL OF PESTS WITH ANNONACEOUS ACETOGENINS

BACKGROUND OF THE INVENTION

Bis(tetrahydrofuranoid) fatty acid lactones, represented by the structural formula,

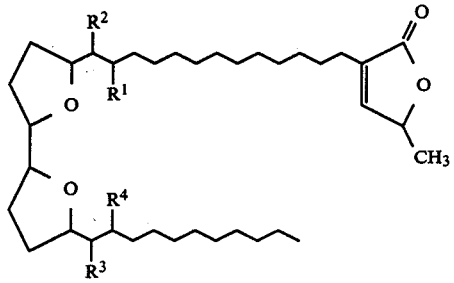
(I)

have been reported in the literature as having cytotoxic and antitumor activity. The first such compound reported [Jolad et al., J. Org. Chem. 47: 3151–3153 (1982)] was called uvaricin and was characterized by an —OH group in the $R^2$ position and an acetoxy group in the $R^3$ position, with $R^1$ and $R^4$ being hydrogen. Uvaricin was isolated from the roots of *Uvaria accuminata* of the family Annonaceae and demonstrated activity in vivo against P-388 lymphocytic leukemia in mice. Jolad et al. [J. Nat. Prod. 48(4): 644–645 (July-August 1985)] discloses the compound desacetyluvaricin which differs from uvaricin in having an hydroxyl in the $R^3$ position. Dabrah et al. [Phytochemistry 23(9): 2013–2016 (1984)] shows the isolation of the stereoisomers rollinicin and isorollinicin from the roots of *Rollinia papilionella* (Annonaceae). These compounds were reported as having —OH in $R^2$, $R^3$, and $R^4$ positions with $R^1$ being hydrogen. Both of these compounds exhibited in vitro cytotoxic activity against the P-388 lymphocytic leukemia. Dabrah et al. [J. Nat. Prod. 47(4): 652–657 (July-August 1984)] discloses another member of the series referred to as rollinone. Rollinone is characterized by a keto group at the $R^1$ carbon, hydroxyls at $R^2$ and $R^3$, and hydrogen for $R^4$ with a saturated lactone ring as illustrated in structure IA:

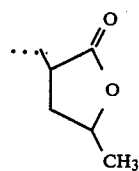
(IA)

Rollinone demonstrated both cytotoxicity against P-388 in vitro and also activity in vivo against the same system in mice. The compounds having the general structure designated by formula I, above, have acquired the name "linear acetogenins."

Cortes et al. [Tetrahedron Lett. 25(30): 3199–3202 (1984)] describe two additional linear acetogenins from *Annona cherimolia* (Annonaceae), wherein the structures are reported as follows:

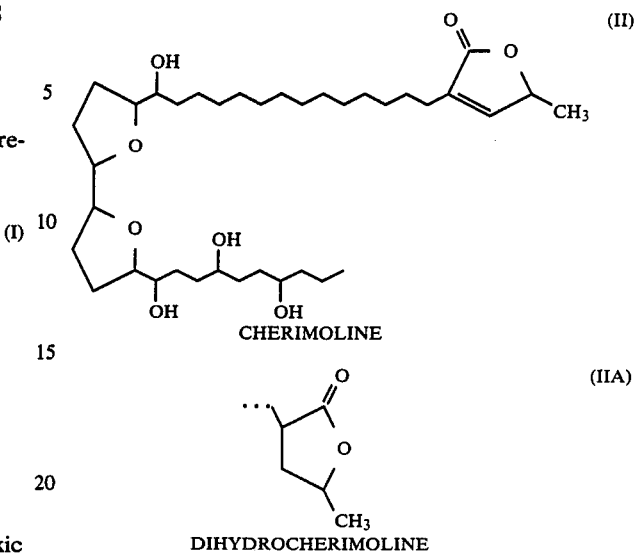

CHERIMOLINE

DIHYDROCHERIMOLINE

These compounds have antimicrobial activity as demonstrated against Gram negative bacteria and Candida.

SUMMARY OF THE INVENTION

We have now discovered that the tetrahydrofuranoid fatty acid lactones (acetogenins) and plant extracts containing these compounds have potent pesticidal and feeding deterrent activity against a diverse variety of pests. These compounds are characterized by the structural formula

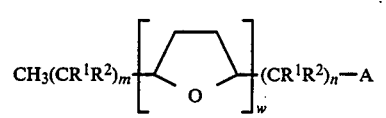
(III)

wherein A is selected from:

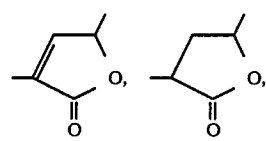

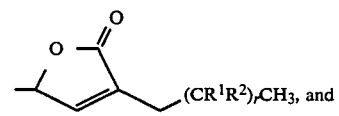

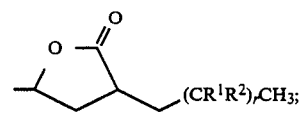

wherein $R^1R^2$ is selected from:

H, H; H, OH; H, OAc; and =O, with the proviso that the total number of oxy substituents for $R^1$ and $R^2$ does not exceed 6; and
wherein:
m=9–15
n=10–18
r=1
w=1 or 2 with the proviso that:
when w=1, m+n+2r is in the range of 25–29; and
when w=2, m+n+2r is in the range of 21–25.

Included within this class of compounds is a novel member named asimicin which has been isolated from the bark and seeds of the pawpaw tree, *Asimina triloba* (Annonaceae).

In accordance with this discovery, it is an object of the invention to define a previously unrecognized class of pest control agents having potential availability from both botanical and synthetic sources.

It is also an object of the invention to provide a new and unobvious use for the annonaceous acetogenins reported in the literature.

Another object of the invention is to introduce the novel acetogenic compound, asimicin, which is characterized by pesticidal and feeding deterrent activities.

A further object of the invention is to identify pesticidal and feeding deterrent activities for the subject series of compounds and for plant extracts containing these compounds against a wide spectrum of pests to include agronomic pests.

Other objects and advantages of this invention will become readily apparent from the ensuing description.

DETAILED DESCRIPTION OF THE INVENTION

Contemplated for use in this invention as pesticidal and feeding deterrent agents are members of a series of linear acetogenic compounds as defined by structural formula III, above, to include mixtures of these compounds and plant extracts comprising them. As shown in formula III, members belonging to this series are generally 35 to 39 carbons in length and are variously hydroxylated, acetylated, or ketonized along the linear alkyl portions of the chain. These compounds possess up to two adjacent tetrahydrofuran rings near the middle of the chain. They are also characterized by a methylated γ-lactone which may be saturated or α,β-unsaturated, and which is either at the end of the chain or is sometimes rearranged to form a new intrachain γ-lactone with another γ-hydroxyl. As noted above in the "Background of the Invention," those compounds of botanical origin previously isolated from annonaceous plants tend to be characterized by the bis(tetrahydrofuranoid) rings, a total of 37 carbons in the main chain, and 2–4 oxy substituents appended to the alkyl moieties of the molecule.

The linear acetogenins of this invention are known to occur in several species of annonaceous plants, to include *Asiminia triloba, Uvaria accuminata, Rollinia papilionella, Rollinia sylvatica, Annona cherimolia,* and *Annona densicoma*. These and other members of the Annonaceae are considered to be suitable sources of the subject compounds. Synthetic methods, as may be developed in the future, could also provide the useful agents.

The newly discovered compound, asimicin, is typical of the annonaceous linear acetogenins and is represented by the following structural formula (IV):

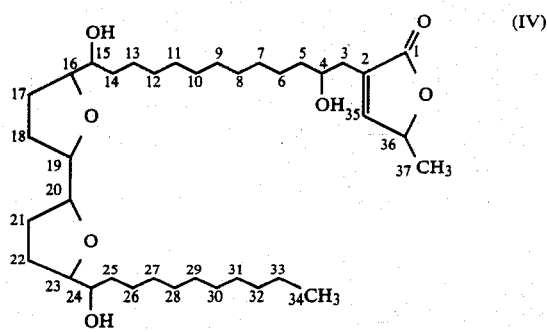

While the findings of this invention have verified the bark and seeds of the pawpaw, *Asimina triloba* Dunal. (Annonacaea) as sources of asimicin, bioassays of ethanolic extracts of the leaves and twigs, skins of fruits, and the wood suggest that the compound is also present in other tissues of the plant. The bark, however, appears to be the most potent plant part. For purposes of illustration, isolation of asimicin from the bark of pawpaw will be presently outlined, and described in further detail in Example 1, below.

As a practical matter, it is envisioned that commercial formulations of the subject pesticidal agents would be prepared directly from plant extracts, or fractions derived from such extracts, thereby obviating the need to isolate the compounds in pure form. It is clear from the fractionation scheme, presented in Example 1 for asimicin, that the linear acetogenins are soluble in aqueous ethanol, aqueous methanol, and dichloromethane. Other suitable solvents could be readily determined by the skilled artisan. Of course, for applications demanding a high degree of specificity, that is, a high level of predictability of the intended response by both target and nontarget organisms, it would normally be preferred to prepare the formulations from pure or substantially pure acetogenins. For example, it is possible that extraneous substances in the natural plant material would have an undesirable masking or antagonistic effect in regard to the intended activity, or a toxic effect toward the nontarget species. These same considerations of purity would be applied to compounds produced synthetically.

The potency of these agents dictates that they be applied in conjunction with a suitable inert carrier or vehicle as known in the art. Of particular interest are those which are agronomically or pharmaceutically acceptable. Alcohols, acetone, chloroform, aqueous alcohol, and aqueous surfactant mixtures are illustrative of suitable carriers. Depending on the substrate, target species, mode of application, and type of response desired, the concentration of active ingredient in the final composition may vary considerably, but typically should be at least about 0.00001% (0.1 p.p.m.). Factors such as phytotoxicity toward the treated plant and tolerance of non-target species can be used by the skilled artisan in determining the maximum level.

Depending on the pest species, concentration of agent, and method of application, the subject acetogenins act to control pests by one or more mechanisms, including, for instance, death inducement, feeding deterrency, growth regulation, sterilization, as well as interference with metamorphosis and other morphogenic functions. Accordingly, the level of active agent is administered in an amount effective to induce one or more of these responses as predetermined by routine testing. Where the ultimate response is pest mortality, an "effective amount" or "pesticidally effective amount" is defined to mean those quantities of agent which will result in a significant mortality rate of a test group as compared to an untreated group. The actual effective amount may vary with the species of pest, stage of larval development, the nature of the substrate, the particular acetogenic agent, the type of vehicle or carrier, the period of treatment, and other related factors.

To be effective, the agent must be applied to the locus of, or the vicinity of, the pest to be controlled. When the agent is intended as a stomach poison or feeding deterrent, it is applied in conjunction with its carrier to the pest diet. In the case of plants, the composition will typically be applied to the leaf surfaces or else systemically incorporated. Alternatively, when the agent is to be used as a contact poison, any method of topical application, such as direct spraying on the pest or on a substrate which is likely to be contacted by the pest, would be appropriate. For purposes of treating internal animal parasites, the agent would be internally administered to the host.

The acetogenic compounds encompassed herein are effective in controlling a wide variety of multicellular organisms. Without desiring to be limited thereto, pests of particular interest known to be vulnerable to treatment are agronomically important insects, especially those of the orders Hemiptera, Coleoptera, and Diptera. Agricultural pests of other phyla including spider mites (Arthropoda) and nematodes are also susceptible to treatment with the subject compounds.

While not desiring to be bound to any particular theory of operation, it is believed that the biological activity is attributed to the lactone ring in combination with the tetrahydrofuranoid ring(s). The oxygenated alkyl segments are thought to be critical to site attachment of the molecule within the target organism.

The following examples are intended only to further illustrate the invention and are not intended to limit the scope of the invention which is defined by the claims.

EXAMPLE 1

Bioassay Procedure

The following bioassay procedure was used to guide the phytochemical fractionation described below.

The $LC_{50}$ of brine shrimp (*Artemia salina* Leach) for each fraction was determined by substantially the same method described in Meyer et al. [Planta Med. 45: 31–34 (1982)]. The test sample was dissolved in solvent and added to 2-dram vials in an amount to provide 1000, 100, 10, 1, etc. p.p.m. of material in the final brine preparation, assuming complete miscibility in the brine. The vials were dried in vacuo, and artificial sea water prepared from a commercial salt mixture was added. Ten brine shrimp larvae (nauplii), 48–72 hrs. old, were introduced to the vial, and the volume was made up to 5 ml. with the sea water. After 24 hrs., the percent mortality was computed, correcting for control deaths using Abbott's formula:

% control =

$$\frac{\% \text{ dead (treated group)} - \% \text{ dead (untreated group)}}{100 - \% \text{ dead (untreated group)}} \times 100$$

Subsequently, $LC_{50}$ values and 95% confidence limits were calculated to permit comparison of potencies of extracts and fractions.

Isolation Procedure

Extraction of Plant Material

Bark of *Asimina triloba* (pawpaw) was freeze dried and ground in a Wiley mill to 2 mm. The ground bark (3.990 kg.) was extracted by exhaustive percolation with 185 l. of 95% ethanol. The ethanol solubles were vacuum evaporated to a syrupy residue which was labeled Fraction F017. Fraction F017 was partitioned between $CH_2Cl_2/H_2O$ (1:1), and the water solubles were taken to dryness and labeled F018. The $CH_2Cl_2$ solubles were recovered as a syrupy residue using a solvent evaporator. This residue was labeled Fraction F019, and a 223-g. sample of F019 was then partitioned between hexane and 90% aqueous methanol. The methanol solubles were thereafter vacuum evaporated to a thickened syrup (41 g.) and labeled as Fraction F020. The recovered hexane solubles constituted Fraction F021.

The results of the brine shrimp bioassay are reported in Table I, below.

Chromatography of Fraction F020

A sample of F020 (39.5 g.), the most toxic partition fraction indicated by the brine shrimp assay (Table I), was absorbed on celite (150 g.) and applied to a silica column (4.0 kg.) packed in benzene/EtOAc (80:20). The column was eluted with 10-l. aliquots of 20%, 50% EtOAc/benzene, 100% EtOAc, 2%, 5%, 20%, 50% MeOH/EtOAc, and finally, 100% MeOH, and fractions were dried and weighed.

A TLC plate was run, in hexane/EtOAc (20:80), on every fifth column fraction and sprayed with 0.5% tetrazolium blue in MeOH:5N NaOH (1:1). From the appearance after TLC, pools of similar compounds were made and the pools assayed against brine shrimp. The results are reported in Table II.

C-18 Column Chromatography of Fraction AT 49

The most active fraction in the brine shrimp assay, AT 42, was consumed in development of a satisfactory separation method. The next most active and comparable fraction, AT 49, was subjected to C-18 column chromatography. AT 49 (1.924 g.) was absorbed on celite (8 g.), applied to the top of a column of C-18 silica (60 g.), and chromatographed and assayed by brine shrimp lethality as shown below in Table III.

TABLE I

| Assay of Partition Fractions from Ethanolic Extracts of the Bark of *Asimina triloba* | |
|---|---|
| F No. | Brine shrimp $LC_{50}$ (p.p.m.) |
| 017 | 7.56 |
| 018 | >1000 |
| 019 | 1.67 |
| 020 | 0.04 |
| 021 | 715 |
| asimicin | 0.03 |

TABLE II

| Column Chromatography Fractions from F020 | | | |
|---|---|---|---|
| Pool No. | Fractions pooled | Weight (g.) | Brine shrimp $LC_{50}$ (μg./ml.) |
| AT 5 | 1–5 | 2.71 | >200 |
| AT 10 | 6–10 | 1.52 | >200 |
| AT 15 | 11–15 | 0.64 | >200 |
| AT 22 | 16–22 | 0.35 | >200 |
| AT 25 | 23–25 | 0.33 | >200 |

TABLE II-continued

| Column Chromatography Fractions from F020 | | | |
|---|---|---|---|
| Pool No. | Fractions pooled | Weight (g.) | Brine shrimp LC$_{50}$ (μg./ml.) |
| AT 32 | 26–32 | 2.70 | >200 |
| AT 36 | 33–36 | 2.04 | 0.15 |
| AT 42 | 37–42 | 2.31 | 0.07 |
| AT 49 | 43–49 | 2.33 | 0.13 |
| AT 55 | 50–55 | 5.12 | 0.85 |
| AT 58 | 56–48 | 0.66 | 1.07 |
| AT 67 | 59–67 | 1.59 | 0.33 |
| AT 71 | 68–71 | 0.45 | 0.49 |
| AT 74 | 72–74 | 2.46 | 0.52 |
| AT 80 | 75–80 | 2.86 | 0.37 |
| AT 88 | 81–88 | 0.47 | 0.52 |
| AT 93 | 89–93 | 0.38 | 0.46 |
| AT 98 | 94–98 | 2.59 | >200 |
| AT 121 | 99–121 | 6.12 | >200 |

TABLE III

| C-18 Column Chromatography of AT 49 | | | |
|---|---|---|---|
| Solvent | Weight (mg.) | Fraction No. | Brine shrimp LC$_{50}$ (μg./ml.) |
| 50% MeOH (100 ml.) | 36.6 | AT 49-1 | 0.30 |
| 60% MeOH (100 ml.) | 30.8 | AT 49-2 | 6.28 |
| 70% MeOH (100 ml.) | 28.9 | AT 49-3 | 4.92 |
| 80% MeOH (100 ml.) | 49.2 | AT 49-4 | 0.37 |
| 90% MeOH (100 ml.) | 832.3 | AT 49-5 | 0.36 |
| MeOH (100 ml.) | 433.5 | AT 49-6 | 0.36 |
| MeOH (100 ml.) | 363.8 | AT 49-7 | 1.0 |

Chromatotron Separation of Fraction AT 49-5

Separation of the most abundant active fraction AT 49-5, which was active in the brine shrimp assay, from the above C-18 column separation of AT 49 (Table III) was carried out as follows. A 4-mm. silica chromatotron rotor was loaded with 586.3 mg. of AT 49-5 and eluted with CHCl$_3$/MeOH/H$_2$O (5:2:2); this resulted in 25 fractions which were then pooled on the basis of their similarities upon TLC analysis (Table IV).

Purification of Fraction AT 49-5-2

A white waxy substance (m.p. 68°–69° C.) precipitated from an Et$_2$O solution of AT 49-5-2 upon the addition of hexane. The precipitate was collected, assayed in five different TLC systems, and visualized with Na$_2$Cr$_2$O$_7$ in 40% H$_2$SO$_4$. Each of the TLC analyses showed only a single spot indicating homogeneity. The collected compound, labeled AT-II (81.35 mg.), was then subjected to structural analyses, including: high resolution FAB MS, IR, UV, $^1$H NMR (CDCl$_3$) with selective $^1$H-$^1$H decouplings, and $^{13}$C NMR. This compound was named "asimicin" and was assigned the structure indicated by formula IV, above.

EXAMPLE 2

Fractions F017, F020, AT 36, and AT 49 from the fractionation of *Asiminia triloba* bark extract described in Example 1 were bioassayed at various levels of test material against a plurality of common agronomic pests.

The southern armyworm (*Spodoptera eridania* Cramer) bioassay was conducted by first applying an aqueous solution of 5000 p.p.m. test material to leaves of a squash plant and allowing the leaves to dry. The leaves were then removed from the plant and placed in petri dishes with the armyworm larvae. The percent mortality was computed from the number of dead larvae after 3 days.

TABLE IV

| Chromatotron Separation of AT 49-5 | | |
|---|---|---|
| Pool No. | Fractions | Weight (mg.) |
| AT 49-5-1 | 1–6 | 25.9 |
| AT 49-5-2 | 7–13 | 342.1 |
| AT 49-5-3 | 14–16 | 136.7 |
| AT 49-5-4 | 17–20 | 58.3 |
| AT 49-5-5 | 21–25 | 20.4 |

The effectiveness of the test fractions against the twospotted spider mite (*Tetranychus urticae* Koch), an arthropod, and the melon aphid (*Aphis gossypii* Glover) was determined by spraying infested leaves of squash plants with aqueous solutions containing 4000 p.p.m. test material and observing the percent mortality after 24 hrs.

Assay against yellow fever mosquito larvae, *Aedes aegypti* (Linnaeus), involved suspending the larvae in an aqueous solution of the test material, at concentrations of 1000 p.p.m. and less, and determining the percent mortality after 24 hrs.

For assaying against the southern corn rootworm, *Diabrotica undecimpunctata* Howardi, Barber, soil samples treated with 300 p.p.m. of test material were placed in conical paper cups having a small opening at the lower apical end. Larvae emerging from the opening were evaluated for percent mortality after 3 days.

In the corn leafhopper (*Dalbulus maidis* Delong et Wolcott) assay, filter paper in the bottom of a petri dish was wetted with the test solution and allowed to dry. Thereafter, the leafhoppers and a measured amount of food were introduced to the dish, and the percent mortality was determined after 24 hrs.

The comparative results of the screening of Fractions F017, F020, AT 36, and AT 49 against the aforementioned test organisms are reported in Table V, below. Significant activities were detected against melon aphid and mosquito larvae, some activity was apparent against two spotted spider mites and corn leafhoppers, and no activity was observed against southern armyworm and corn rootworm.

EXAMPLE 3

Fractions F017, F018, F019, and F020 from the fractionation of *Asimina triloba* bark extract described in Example 1 were bioassayed against mosquito larvae, southern corn rootworm, the southern armyworm, the twospotted spider mite, and the melon aphid by the same procedures described in Example 2. Generally, brine shrimp lethality paralleled the insecticidal activities. In addition, these fractions were assayed against blowfly larvae (*Colliphora vicina* Meig) and the nematode (*Caenorhabditis elegans*).

TABLE V

| Assay of Pawpaw (*Asimina triloba*) Fractions Against Agronomic Pests | | | | | | | |
|---|---|---|---|---|---|---|---|
| | | % Mortality[a,b] | | | | | |
| Fraction | Concentration (p.p.m.) | Southern armyworm | Twospotted spider mite | Melon aphid | Mosquito larvae | Southern corn rootworm | Corn leafhopper |
| F017 | 200 | 10 | 0 | 0 | — | — | — |
| | 20 | — | — | — | 50 | — | — |

TABLE V-continued

Assay of Pawpaw (*Asimina triloba*) Fractions Against Agronomic Pests

| Fraction | Concentration (p.p.m.) | % Mortality[a,b] | | | | | |
|---|---|---|---|---|---|---|---|
| | | Southern armyworm | Twospotted spider mite | Melon aphid | Mosquito larvae | Southern corn rootworm | Corn leafhopper |
| | 12 | — | — | — | — | 0 | — |
| F020 | 200 | 0 | 0 | 30 | — | — | — |
| | 20 | — | — | — | 100 | — | — |
| | 12 | — | — | — | — | 0 | — |
| AT 36 | 200 | 0 | 10 | 90 | — | — | — |
| | 100 | — | — | — | — | — | 10 |
| | 20 | — | — | — | 100 | — | — |
| | 12 | — | — | — | — | 0 | — |
| AT 49 | 200 | 0 | 10 | 90 | — | — | — |
| | 100 | — | — | — | — | — | 0 |
| | 20 | — | — | — | 100 | — | — |
| | 12 | — | — | — | — | 0 | — |

[a] "—" indicates not tested.
[b] The results are corrected for control deaths by Abbott's Formula.

The blowfly larvae assay was conducted by dipping a gauze dental wick into bovine serum containing 1% (w/v) test material. The larvae were thereafter introduced to the wick and evaluated for percent mortality after 24 hrs.

The nematode (*C. elegans*) bioassay was conducted by suspending the worms in a 0.1% (w/v) aqueous solution of the test material and determining the percent mortality after 3 days.

The results of this bioassay series are reported in Table VI, below.

EXAMPLE 4

The activities of Fractions F020, AT 49, and purified asimicin obtained in Example 1 were compared to the commercial pesticides pyrethrum (57%) and rotenone (97%) in assays against the Mexican bean beetle (*Epilachna varivestis* Mulsant), the melon aphid, mosquito larvae, the nematode *C. elegans*, and blowfly larvae.

The Mexican bean beetle assay was conducted by spraying the material onto bean leaves, allowing the leaves to dry, and then introducing the third-instar beetles to the leaves in an enclosed chamber. After 72 hrs., the percent mortality was determined. The assays on the remaining systems were conducted as previously described in Examples 2 and 3. The results are reported in Table VII, below.

EXAMPLE 5

The compound asimicin isolated from the seeds of *Asimina triloba* was assayed by two separate methods against the striped cucumber beetle (*Acalymma vittatum* F.) as described below:

TABLE VI

Assay of Pawpaw (*Asimina triloba*) Fractions Against Agronomic Pests

| | % Mortality[a] | | | | | | | | |
|---|---|---|---|---|---|---|---|---|---|
| | Mosquito larvae | | | | Blowfly larvae, 1% | *C. elegans,* 1% | Southern corn rootworm, 300 p.p.m. | Southern armyworm, 5000 p.p.m. | Twospotted spider mite, 5000 p.p.m. | Melon aphid, 5000 p.p.m. |
| Fraction | 1000 p.p.m. | 100 p.p.m. | 10 p.p.m. | 1 p.p.m. | | | | | | |
| F017 | 100 | 90 | 0 | 0 | 0 | 100 | 0 | 0 | 30 | 0 |
| F018 | 50 | 0 | 0 | 0 | 0 | 0 | 0 | 0 | 0 | 0 |
| F019 | 100 | 100 | 70 | 0 | 100 | 100 | 0 | 0 | 40 | 20 |
| F020 | 100 | 100 | 100 | 80 | 100 | 100 | 0 | 0 | 60 | 50 |

[a] The results are corrected for control deaths by Abbott's Formula.

TABLE VII

Comparative Activities of Pawpaw (*Asimina triloba*) Fractions, Asimicin, and Standard Insecticides

| Treatment material | Rate, p.p.m. | % Mortality[a,b] | | | | |
|---|---|---|---|---|---|---|
| | | Mexican bean beetle, 72 hr. | Melon aphid, 24 hr. | Mosquito larvae, 24 hr. | Nematode, 72 hr. | Blowfly larvae, 24 hr. |
| F020 | 5000 | 100 | 80 | — | — | — |
| | 1000 | 100 | 0 | 100 | 100 | 100 |
| | 500 | 100 | 0 | — | — | — |
| | 100 | 60 | 0 | 100 | 100 | 0 |
| | 10 | — | — | 80 | 100 | 0 |
| | 1 | — | — | 10 | 0 | — |
| AT 49 | 5000 | 100 | 90 | — | — | — |
| | 1000 | 100 | 0 | 100 | 100 | 100 |
| | 500 | 100 | 0 | — | — | — |
| | 100 | 100 | 0 | 100 | 100 | 0 |
| | 10 | — | — | 100 | 100 | 0 |
| | 1 | — | — | 50 | 100 | — |
| Asimicin (purified) | 1000 | — | — | — | — | 100 |
| | 500 | 100 | 100 | — | — | — |
| | 100 | 100 | 20 | 100 | 100 | 0 |

TABLE VII-continued

Comparative Activities of Pawpaw (*Asimina triloba*) Fractions, Asimicin, and Standard Insecticides

| Treatment material | Rate, p.p.m. | % Mortality[a,b] | | | | |
|---|---|---|---|---|---|---|
| | | Mexican bean beetle, 72 hr. | Melon aphid, 24 hr. | Mosquito larvae, 24 hr. | Nematode, 72 hr. | Blowfly larvae, 24 hr. |
| | 50 | 100 | 0 | — | — | — |
| | 10 | 70 | 0 | 100 | 100 | 0 |
| | 1 | — | — | 100 | 100 | 0 |
| | 0.1 | — | — | 0 | 100 | — |
| Pyrethrum (57% pure) | 500 | 100 | 100 | — | — | — |
| | 100 | 100 | 100 | 100 | 0 | 100 |
| | 50 | 100 | 100 | — | — | — |
| | 10 | 0 | 20 | 100 | 0 | 0 |
| Rotenone (97% pure) | 1000 | — | — | — | — | 100 |
| | 500 | — | 0 | — | — | — |
| | 100 | — | — | 100 | 0 | — |
| | 10 | — | — | 50 | — | — |
| | 1 | — | — | 0 | — | — |

[a]"—" indicates not tested.
[b]The results are corrected for control deaths by Abbott's Formula.

Two-Choice Leaf Disc Bioassays

Appropriate quantities of the test material were suspended in acetone, diluted with water containing 0.01% of Tween 20 to a sample concentration of 0.5% (w/v), and then emulsified with a Brinkman Polytron homogenizer. The 0.1% solutions were derived by dilution of the 0.5% solution. Leaf discs (2.0 cm. diameter) cut from "Burpee Hybrid" cantaloupe leaves were dipped in either the sample homogenate or a corresponding homogenate containing no sample (control discs), air dried, and then two of each type of disc were arranged alternately around 93 mm. diameter×73 mm. deep polyethylene dishes. Five newly emerged female striped cucumber beetles, after being starved for 24 hrs., were introduced into each chamber, and the chambers were covered with muslin; these covers were kept moist during the first 6 hrs. of the bioassay by misting them periodically with water. Tests were conducted in two replicates under ambient greenhouse conditions. Observations were made at 3, 6, and 22 hrs. to estimate visually the amount of leaf tissue consumed and to check for deaths.

Data are presented as a consumption index, which is defined as percentage of treated discs consumed×100/(percentage of control discs consumed+percentage of treated discs consumed). A value of 50 indicates treated and untreated discs have been consumed in equal amounts; an extract that gives an index of 20 or less is considered highly deterrent in these bioassays.

No-Choice Leaf Disc Bioassay

For the no-choice feeding study, homogenate samples preparation (0.5% w/v solutions only), leaf disc (1.5 cm. diameter) treatment and drying, and insect preparation were as described for the two-choice bioassay. Single treated discs were placed in individual 2-dram glass vials, and one beetle was introduced into each vial. Water was provided by a soaked 0.5-cm. length of dental wick, and the vials were stoppered with cotton plugs. The bioassays were conducted in 10 replicates under ambient greenhouse conditions; leaf consumption and mortality data were taken daily for 3 days. Data are presented as percent of leaf discs consumed.

The results of the two-choice and no-choice leaf disc bioassays are reported in Tables VIII and IX, below.

It is understood that the foregoing detailed description is given merely by way of illustration and that modification and variations may be made therein without departing from the spirit and scope of the invention.

TABLE VIII

Striped Cucumber Beetle Two-Choice Assay for Asimicin

| Asimicin concentration, % | Consumption index[a] | | |
|---|---|---|---|
| | 3 hr. | 6 hr. | 22 hr. |
| 0.1 | 25 | 20 | 14 |
| 0.5 | 0 | 0 | 0 |

[a]Value of 50 means that equal amounts of treated and control discs were consumed. Value of 0 means that none of the treated disc was consumed.

TABLE IX

Striped Cucumber Beetle No-Choice Assay for Asimicin

| Treatment | Leaf consumed, % | | | Mortality, % | | |
|---|---|---|---|---|---|---|
| | 1 day | 2 days | 3 days | 1 day | 2 days | 3 days |
| Asimicin (0.5%) | 0 | 0 | 0 | 40 | 50 | 50 |
| Control | 31 | 59 | 74 | 0 | 0 | 0 |

We claim:

1. A method for controlling pests selected from the group of insects, arthropods, and nematodes comprising applying to a locus of said pests an effective amount of a compound having the structural formula:

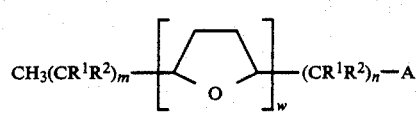

wherein A is selected from:

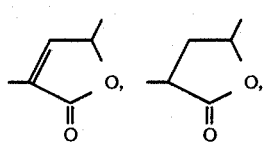

-continued

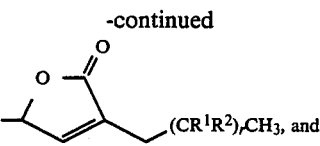

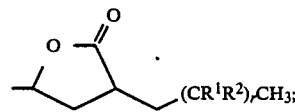

wherein R¹R² is selected from:
H, H; H, OH; H, OAc; and =O,
with the proviso that the total number of oxy substituents for R¹ and R² does not exceed 6; and
wherein:
m=9-15
n=10-18
r=1
w=1 or 2
with the proviso that:
when w=1, m+n+2r is in the range of 25-29; and
when w=2, m+n+2r is in the range of 21-25.

2. The method as described in claim 1 wherein $m+n+2r=27$.

3. The method as described in claim 2 wherein w=2.

4. The method as described in claim 3 wherein A is selected from

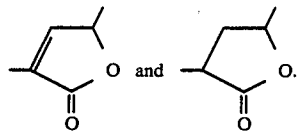

5. The method as described in claim 1 wherein said compound is asimicin.

6. The method as described in claim 1 wherein said pests are insects.

7. The method as described in claim 1 wherein said pests are nematodes.

8. The method as described in claim 1 wherein said pests are arthropods.

9. The method as described in claim 1 wherein said compound is a component of a mixture of said compounds.

10. The method as described in claim 5 wherein said compound is a component of a mixture of said compounds.

11. The method as described in claim 1 wherein said compound is a component of an annonaceous plant extract.

12. The method as described in claim 5 wherein said compound is a component of an annonaceous plant extract.

13. A method as described in claim 1 wherein said compound is applied to the substrate in combination with a suitable carrier.

* * * * *